US011459375B2

(12) United States Patent
Holthoff et al.

(10) Patent No.: US 11,459,375 B2
(45) Date of Patent: Oct. 4, 2022

(54) CYCLIC PEPTIDES FOR THE TREATMENT OF GRAVES' DISEASE

(71) Applicant: advanceCOR GmbH, Martinsried (DE)

(72) Inventors: Hans-Peter Holthoff, Martinsried (DE); Martin Ungerer, Martinsried (DE); Julia Fassbender, Martinsried (DE); Zhongmin Li, Martinsried (DE)

(73) Assignee: advanceCOR GmbH, Martinsried (DE)

( * ) Notice: Subject to any disclaimer, the term of this patent is extended or adjusted under 35 U.S.C. 154(b) by 261 days.

(21) Appl. No.: 16/490,358

(22) PCT Filed: Feb. 28, 2018

(86) PCT No.: PCT/EP2018/054919
§ 371 (c)(1),
(2) Date: Aug. 30, 2019

(87) PCT Pub. No.: WO2018/158310
PCT Pub. Date: Sep. 7, 2018

(65) Prior Publication Data

US 2020/0071384 A1 Mar. 5, 2020

(30) Foreign Application Priority Data

Mar. 1, 2017 (EP) .................................... 17158652

(51) Int. Cl.
*A61K 39/00* (2006.01)
*C07K 14/72* (2006.01)
*A61P 5/06* (2006.01)
*A61K 38/00* (2006.01)

(52) U.S. Cl.
CPC .............. *C07K 14/723* (2013.01); *A61P 5/06* (2018.01); *A61K 38/00* (2013.01); *A61K 39/0008* (2013.01)

(58) Field of Classification Search
None
See application file for complete search history.

(56) References Cited

FOREIGN PATENT DOCUMENTS

| | | |
|---|---|---|
| WO | WO 2008/091981 A2 | 7/2008 |
| WO | WO 2009/007848 A2 | 1/2009 |
| WO | WO 2015/019302 A2 | 2/2015 |

OTHER PUBLICATIONS

Uniprot entry for TSHR, downloaded Feb. 23, 2021.*
Hofflich, Heather; "Patients with hashimoto's thyroiditis and negative thyroid antibodies have a milder form of the disease." Clin. Thyroidology Public (2014) 7(9) p. 10-11.*
Intenzo, Charles M. et al; "Scintigraphic manifestations of thyrotoxicosis." Radiographics (2003) 23 p. 857-869.*
Bagriacik, E. Umit and Klien, John R.; "They thyrotropin (thyroid stimulating hormone) receptor is expresson on murine dendritic cells and on a subset of cd45rbhigh lymph node t cells: functional role for thryorid stimulating hormone during immune activation." J. Immunol. (2000) 164 p. 6158-6165.*
International Search Report and Written Opinion dated Apr. 17, 2018 in PCT/EP2018/055635 filed Feb. 28, 2018.
Ungerer et al., "Reivew of Mouse Models of Graves' Disease and Orbitopathy-Novel Treatment by Induction of Tolerance," Clinical Reviews in Allergy and Immunology, Humana Press, Totowa, NJ, vol. 52, No. 2, Jul. 2, 206, pp. 182-193.
Boivin et al., "Novel Receptor-Derived Cyclopeptides to Treat Heart Failure Caused by Anti-[beta]1-Adrenoceptor Antibodies in a Human-Analogous Rat Model," PLOS ONE, vol. 10, No. 2, Feb. 20, 2015 p. e0117589.
Holthoff et al., "Cyclic Peptides for Effective Treatment in a Long Term Model of Graves' Disease and Orbitopathy in Female Mice," Endocrinology, Mar. 29, 2017.

* cited by examiner

*Primary Examiner* — Fred H Reynolds
(74) *Attorney, Agent, or Firm* — Williams Mullen; David M. Saravitz

(57) ABSTRACT

The present invention relates to a cyclic peptide, its use in the treatment, amelioration or prevention of a disease caused by antibodies targeting the thyrotropin-TSH receptor (TSHR) in the thyroid gland, in particular Graves' disease and orbitopathy, and to pharmaceutical compositions comprising the same.

7 Claims, 8 Drawing Sheets

Specification includes a Sequence Listing.

A

B

A

- → i.m. immunisations / ECG to measure heart rates
- ⇢ i.v. administration of peptides / vehicle (NaCl)
- \* blood withdrawals
- ° determination of T4 and/or anti-TSHR antibodies from serum samples
- # final ECG reordings / thyroid and orbital histopathology

B

A

B

A

B

A

B

```
                         SEQUENCE LISTING


<160> NUMBER OF SEQ ID NOS: 10

<210> SEQ ID NO 1
<211> LENGTH: 24
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 1

Gly Tyr Ala Phe Asn Gly Thr Lys Leu Asp Ala Val Tyr Leu Asn Lys
1               5                   10                  15

Asn Lys Tyr Leu Thr Val Ile Asp
            20


<210> SEQ ID NO 2
<211> LENGTH: 24
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 2

Ser Pro Pro Cys Glu Cys His Gln Glu Glu Asp Phe Arg Val Thr Cys
1               5                   10                  15

Lys Asp Ile Gln Arg Ile Pro Ser
            20


<210> SEQ ID NO 3
<211> LENGTH: 24
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 3

Leu Pro Pro Ser Thr Gln Thr Leu Lys Leu Ile Glu Thr His Leu Arg
1               5                   10                  15

Thr Ile Pro Ser His Ala Phe Ser
            20


<210> SEQ ID NO 4
<211> LENGTH: 17
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 4

Ser Asn Leu Pro Asn Ile Ser Arg Ile Tyr Val Ser Ile Asp Val Thr
1               5                   10                  15

Leu


<210> SEQ ID NO 5
```

```
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 5

Tyr Asn Leu Ser Lys Val Thr His Ile Glu Ile Arg Asn Thr Arg Asn
1               5                   10                  15

Leu Thr Tyr Ile Asp Pro Asp Ala
            20


<210> SEQ ID NO 6
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 6

Leu Lys Glu Leu Pro Leu Leu Lys Phe Leu Gly Ile Phe Asn Thr Gly
1               5                   10                  15

Leu Lys Met Phe Pro Asp Leu Thr
            20


<210> SEQ ID NO 7
<211> LENGTH: 17
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 7

Lys Val Tyr Ser Thr Asp Ile Phe Phe Ile Leu Glu Ile Thr Asp Asn
1               5                   10                  15

Pro


<210> SEQ ID NO 8
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 8

Asn Ala Phe Gln Gly Leu Cys Asn Glu Thr Leu Thr Leu Lys Leu Tyr
1               5                   10                  15

Asn Asn Gly Phe Thr Ser Val Gln
            20


<210> SEQ ID NO 9
<211> LENGTH: 20
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 9

Lys Asp Ala Phe Gly Gly Val Tyr Ser Gly Pro Ser Leu Leu Asp Val
1               5                   10                  15
```

-continued

```
Ser Gln Thr Ser
            20


<210> SEQ ID NO 10
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 10

Pro Ser Lys Gly Leu Glu His Leu Lys Glu Leu Ile Ala Arg Asn Thr
1               5                   10                  15

Trp Thr Leu Lys Lys Leu Pro Leu
            20
```

CYCLIC PEPTIDES FOR THE TREATMENT OF GRAVES' DISEASE

CROSS-REFERENCE TO RELATED APPLICATIONS

This application is the U.S. National Stage of International Application PCT/EP2018/054919, filed Feb. 28, 2018, which designates the U.S and was published by the International Bureau in English on Sep. 7, 2018, and which claims the benefit of European Patent Application No. 17 158 652.2, filed Mar. 1, 2017; all of which are hereby incorporated herein in their entirety by reference.

FIELD OF THE INVENTION

The present invention relates to a cyclic peptide, its use in the treatment, amelioration or prevention of a disease caused by antibodies targeting the thyrotropin-TSH receptor (TSHR) in the thyroid gland, in particular Graves' disease and orbitopathy, and to pharmaceutical compositions comprising the same.

BACKGROUND OF THE INVENTION

Graves' disease is a common antibody-mediated autoimmune condition targeting the thyrotropin-TSH receptor (TSHR) in the thyroid gland, resulting in hyperthyroidism (1), with an annual incidence of 15-80 per 100,000 persons throughout the world. The disease is often initially treated by giving thyreostatic drugs, such as carbimazol, followed by radioiodine therapy (2) or surgical removal of the thyroid gland. All these treatment options are characterized by relatively high relapse rates, and significant side effect profiles (3). A quality of life (QOL) assessment showed that all options are accompanied by a reduced vital and mental QOL even many years after treatment (4). If left untreated, Graves' leads to significantly increased morbidity and mortality (4).

Treatments of refractory disease cases and of accompanying ophthalmopathy/orbitopathy are especially challenging. Ophthalmopathy occurs in almost half of all Graves' patients—up to 16 per 100,000 women per year in the general population (5). In this condition, anti-TSHR antibody titers and relapse rates are especially high (5). These patients must frequently be treated with high doses of intravenous corticoids over many weeks, which even incur more side effects (9). Therefore, novel treatment options have been explored in recent years. A reduction of B lymphocytic cell counts can be achieved by giving the anti-CD20 antibody rituximab (MabThera®, anti-CD20 Mab). Driven by the hypothesis that Graves' disease is majorly a B cell-mediated condition, several smaller observational studies (6,7) investigated administration of rituximab in patients with refractory Graves' ophthalmopathy. Two recent randomized double-blind trials yielded disparate results: one showed an advantage for the rituximab-treated group (8), whereas the other did not (NCT 00595335, ref. 9), perhaps due to frequent side effects of the therapy.

Since these approaches did not yield a clear clinical efficacy, and many potential patients declined to participate in the trial for fear of side effects (9), an alternative promise is offered by specific immune therapies which have been established for the treatment of allergic autoimmune conditions for more than 100 years (reviewed e.g. in 10, 11). Increasingly, recombinant peptides are being used for this hyposensitization therapy which offer significant advantages over the classical raw allergen extracts (10,12,13). In general, treatment with broad-range immunosuppressive drugs may cause serious side effects, so that such allergen-specific therapies are conceived to induce tolerance in a variety of related conditions. As a novel option, the intravenous administration of fairly high doses of immunogen-mimicking cyclic peptides for the treatment of anti-G protein-coupled receptor (GPCR)-mediated autoimmune disease has been suggested (14-18).

A disease model for human Graves' disease was established with up to three immunizations with recombinant adenovirus expressing the full-length human TSHR (19), and reconfirmed in further studies using the extracellular A subunit of the TSHR (20). Subsequent studies showed variations of protocol and successful extension upon repeated immunizations (21, 22). This extended protocol of adenovirally induced TSH receptor immunization (22) in which regular injections are continued for nine months, was used to permanently boost antibody production in mice. The model establishes a stable disease phenotype during the whole observation period, including thyroid enlargement (goiter), hyperthyreotic T4 values, tachycardia and retroorbital fibrosis. The latter read-out indicates the severity of ophthalmopathy, as investigated by histological serial orbital sections (23).

SUMMARY OF THE INVENTION

In view of the above, it is the problem of the present invention to provide a polypeptide which is suitable for the treatment, amelioration or prevention of a disease caused by antibodies targeting the thyrotropin-TSH receptor (TSHR) in the thyroid gland, in particular Graves' disease and orbitopathy.

The present invention provides cyclic peptides. Theses cyclic peptides may be used in the treatment or prevention of a disease caused by antibodies targeting the thyrotropin-TSH receptor (TSHR) in the thyroid gland, in particular Graves' disease and orbitopathy.

The present invention provides cyclic peptides comprising the amino acid sequence GYAFNGTKLDAVYLNKNKYLTVID (SEQ ID NO: 1), or a derivative thereof. Suitable derivatives are such, wherein one or two amino acids have been replaced by another amino acid or have been removed. Preferably the cyclic peptide is of formula (I)

cyclo($x_{(i)}$GYAFNGTKLDAVYLNKNKYLTVID (SEQ ID NO: 1)) (I)

wherein x is, at each occurrence, individually selected from an amino acid;

i is an integer from 0 to 5, and derivatives thereof, wherein one or two amino acids have been replaced by another amino acid or have been removed.

Further, the present invention provides a pharmaceutical composition comprising said cyclic peptides, and optionally a pharmaceutically acceptable carrier. The cyclic peptide and the pharmaceutical composition are used for the treatment, amelioration or prevention of a disease caused by antibodies targeting the thyrotropin-TSH receptor (TSHR) in the thyroid gland, in particular for the treatment, amelioration or prevention of Graves' disease, Graves' orbitopathy, Hashimoto's disease and/or hyperthyroidism as well as cardiovascular symptoms associated therewith.

BRIEF DESCRIPTION OF THE DRAWINGS

FIG. 1A shows a time schedule of the study comprising immunizations and therapy.

FIG. 4 A shows representative macroscopic images; FIG. 4 B shows the effect on macroscopically measured thyroid size.

FIG. 6 A shows representative macroscopic images; FIG. 6 B shows digitized analysis of retroorbital tissue.

DESCRIPTION OF THE PREFERRED EMBODIMENTS

Figure 1:
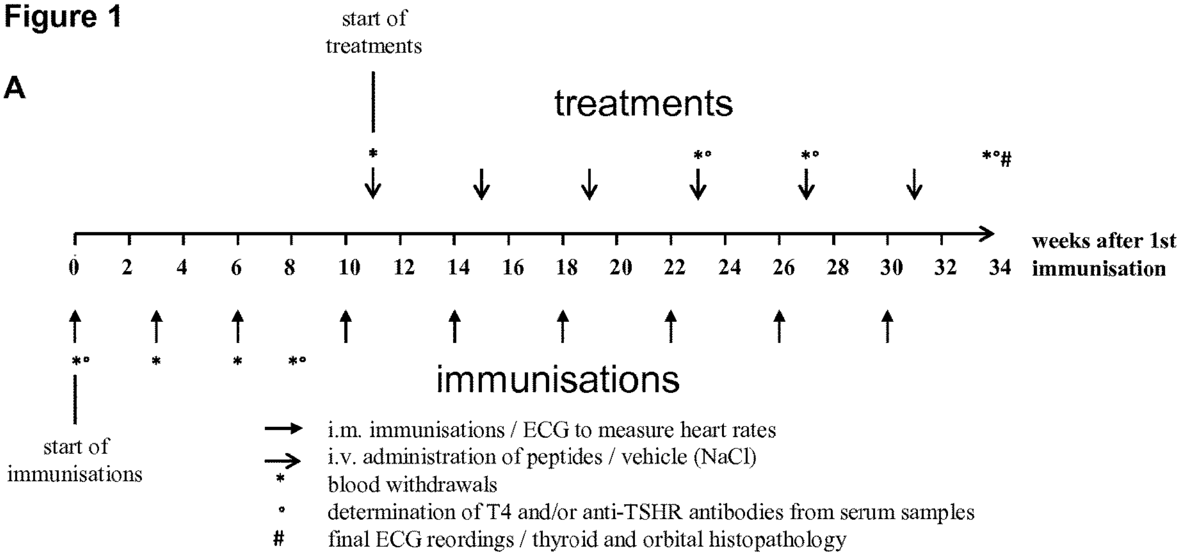
FIG. 1 B shows a schematic structure of the thyroid stimulating hormone (TSH) receptor.
Figure 1:
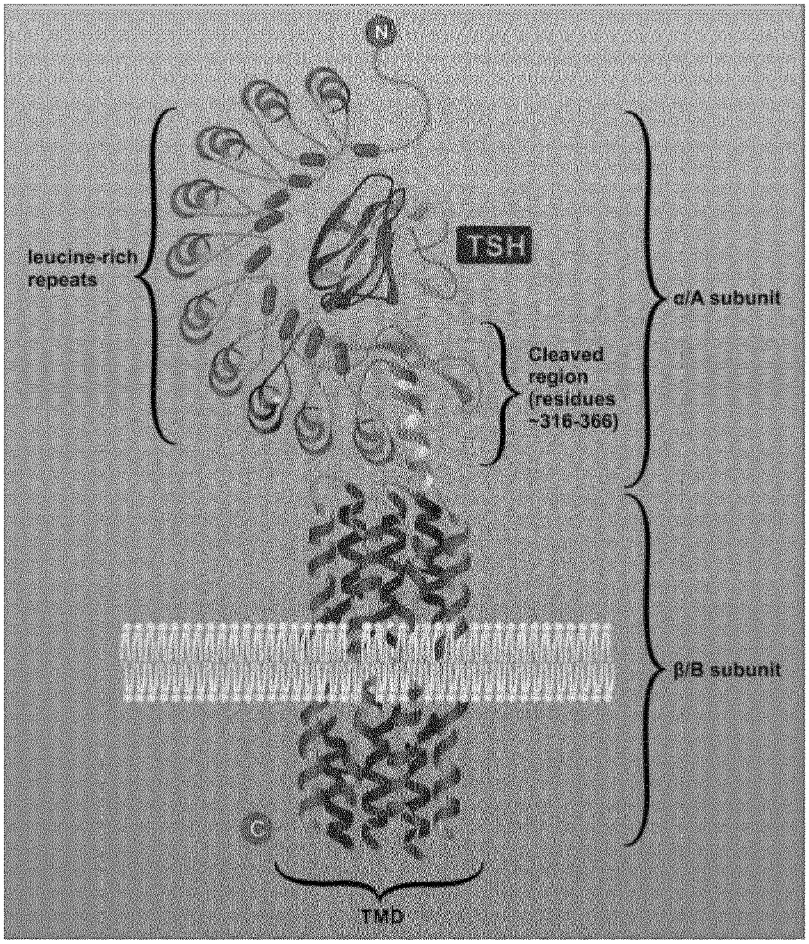

The present invention provides cyclic peptides comprising the amino acid sequence GYAFNGTKLDAVYLNKNKYLTVID (SEQ ID NO. 1), or a derivative thereof. Preferably the cyclic peptide is of formula (I)

$$\text{cyclo}(x_{(i)}\text{GYAFNGTKLDAVYLNKNKYLTVID}) \quad \text{(I)}$$

wherein x at each occurrence is individually selected from an amino acid. The integer i is in the range from 0 to 5, i.e. in addition to the peptide of SEQ ID NO. 1 the cyclic peptide may comprise up to 5 additional amino acids in the cyclus.

The invention also relates to derivatives of the cyclic peptide, wherein one or two amino acids, preferably one or two amino acids of SEQ ID NO. 1, have been replaced by another amino acid or have been removed. Typically, the cyclic peptide comprises at least 24 amino acids. Preferably, the cyclic peptide of the invention comprises the unaltered peptide of SEQ ID NO. 1, more preferably index i=0.

The peptide is a cyclic peptide. Cyclic peptides can be obtained by cyclization of linear peptides, which are available by methods of peptide synthesis known in the art, e.g. solid phase peptide synthesis. The cyclization may occur by a linkage which is a covalent binding selected from the group comprising S—S linkages, peptide bonds, carbon bonds such as C—C or C═C, ester bonds, ether bonds, azo bonds, C—S—C linkages, C—N—C linkages and C═N—C linkages. In one embodiment the S—S linkage is formed by two Cys residues of the peptide.

In a preferred embodiment the cyclization occurs by a peptide bond. Preferably, the peptide bond is formed by the NH2 group of the N-terminal amino acid and the COOH group of the C-terminal amino acid. Methods for such cyclization are well known in the art.

In an alternative embodiment additional bonds are formed by the side chain of NH2 groups and COOH groups of the constituent amino acids.

Without wishing to be bound by any theory in the following, the present inventors have surprisingly found that a number of cyclic peptides are suitable for the treatment, amelioration or prevention of a disease caused by antibodies targeting the thyrotropin-TSH receptor (TSHR) in the thyroid gland, in particular for the treatment, amelioration or prevention of Graves' disease, Graves' orbitopathy and/or hyperthyroidism. In particular, it has been found that cyclic peptides which mimic one of the cylindrical loops of the leucine-rich repeat domain of TSHR suppressed or at least stabilized the titers of TSH binding antibodies despite continuing immunisations. Thus, established thyroid disease was successfully treated in animals, and thyroid hyperplasia and histological alterations were markedly reduced. Elevated thyroxin (T4) levels were reverted to normal values, starting 15 weeks after initiation of peptide therapy. It is also shown that retro-orbital fibrosis was minimized, suggesting a positive effect on Graves' orbitopathy. Tachycardia and cardiac hypertrophy were consistently reduced by the novel therapy.

In more detail, the present invention is based on the finding that a specific cyclic peptide which mimics the eighth cylindrical loop of the leucine-rich domain of TSHR markedly reduced thyroid hyperplasia and histological alterations in a long-term mouse model of Graves' disease. Elevated thyroxin (T4) levels were reverted to normal values, starting 15 weeks after initiation of peptide therapy. It has also been found that retro-orbital fibrosis, tachycardia and cardiac hypertrophy were consistently reduced after repeated administration of the novel peptides. Although treatment with both, the cyclic peptide of the invention and a fully antigenic fusion protein of the TSHR A subunit and IgG-Fc (TSHR-Fc) suppressed or at least stabilized the titers of TSHR binding antibodies despite continuing immunizations, TSHR-Fc treatment led to clinical signs of allergic reactions in immunized mice which had to be treated by administration of the anti-histaminic agent clemastin. Also comparing the two treatments in naïve mice reconfirmed that the shorter cyclic peptides are not immunogenic on their own, whereas administration of TSHR-Fc led to induction of anti-TSHR antibodies and clinical signs of allergy in some animals.

In contrast, treatment with a different cyclic peptide designed in analogy to another loop of the subunit A of TSHR only resulted in small, non-significant trends, and other peptides mimicking the remaining loops of the TSHR leucine-rich domain did not result in any effects at all.

Addition of serum samples from in vivo treated mice to measure the maximum TSHR-induced cAMP levels in test cells showed that this parameter was not affected by either therapy with the cyclic peptide in accordance with the invention nor TSHR-Fc. Spiking of TSHR-Fc, but not of the cyclic peptides to anti-TRSR antibodies ex vivo resulted in a reduction of titer and activity, suggesting an antibody-scavenging capacity of TSHR-Fc, but not of the peptides. Their interaction with immune mechanisms in vivo might be based on direct B cell or T cell effects. Long-term repeated adenovirally induced TSH receptor A subunit immunization in mice leads to a long-term model of Graves' disease. This model was used to test therapeutic approaches based in the cyclic peptide in accordance with the invention. Previous studies in Ad-TSHR-immunized mice had established that the model can be used to investigate therapeutic interventions.

Concerning the potential modes of action of the cyclic peptides, a variety of hypotheses might be considered: The immune-modulating potency of cyclic peptides which mimic parts of the antigen may depend on their property that they may be presented to the immune system via major histocompatibility class II (MHC II)-dependent antigen-presenting cells without a co-stimulatory signal, and thereby reduce immune activation. In this process, possible intermediate steps include the induction of T reg regulatory lymphoid cells, the suppression of Th 1 and the promotion of Th 2 responses. These phenomena have been described during the hyposensitization with specific peptides, such as for the major cat allergen Fel D1 (39, 13). Parallel induction of blocking IgG4 vs IgE has been documented (13,38), but can unfortunately not be studied in mice (11).

An alternative explanation for the observed phenomena would be a complete and direct B cell anergy by impacting on peripheral lymphoid organs, which can also be observed with the broader, less specific approaches of generally blocking co-stimulatory signals or B cell depletion (reviewed e. g. in 40, 49). This is also assumed to be the major effect of cyclic peptides which suppress anti-β1AR antibodies raised in rats (16).

With regard to the anti-TSHR antibody titer assays, the current gold standard "3rd generation" immunoassay, which detects the ability of the respective mouse sera to inhibit the binding of the monoclonal Graves' patient antibody M22 to the TSHR (RSR-Cobas Roche), is most often used to identify Graves' disease in humans. This assay was reported to identify Graves' patients with a specificity and sensitivity of >97% (42, 43). The present invention documents effects of novel therapies on the anti-TSHR antibody titers which were measured by the same assay as used in human patients. In contrast, the peptides showed no or very little effect on TSHR-mediated cAMP stimulatory potency during progressive therapy (see FIG. 3)—other second messenger pathways coupled to TSHR might be involved, such as Gq—PLC or even Gi.

In addition, orbital histology and quantified retro-orbital fibrosis was investigated by digitized image analysis, which represents an important hallmark of clinical disease in humans. It has been shown to be altered in prior studies using electroporation and plasmid gene transfer (44, 45), but not during short-term adenoviral TSHR immunisation (46). In contrast, a previous study showed that Graves' orbitopathy develops if adenoviral immunisations are maintained for several months (23). The administration of the novel cyclic peptides of the invention induced a significant reduction of retro-orbital fibrosis in the current study. Such a therapeutic effect has not yet been shown in animal models. On the other hand, patients with Graves ophthalmopathy are especially hard to treat.

Also the effect of the novel peptides on the cardiac manifestations and complications of Graves' disease was investigated. Tachycardia is a reliable marker of disease severity in hyperthyroid patients (47,48). 24 h ECG monitoring showed that heart rate is constantly increased during the day (48). Therefore, we sought to examine whether the investigated immune treatments can also impact on the clinically important cardiac involvement in this animal model. Regular ECG registrations served to detect the effect on heart rate. Treatment with either TSHR-Fc or the cyclic peptide of the invention significantly decreased the tachycardia which progressively developed in untreated TSHR-immunized mice over 3-9 months.

In summary, it is shown that treatment of clinical disease manifestations in this mouse model of Graves' disease led to marked improvement of all disease parameters. TSHR-Fc resulted in direct antibody scavenging ex vivo, but induced allergic reactions in some animals in vivo. The LRR loop-mimicking cyclic peptide according to the invention was equally effective in vivo, but did not show this ex vivo effect. Since it mimics a part of the antigenic receptor, it might be presented to the immune system via major histocompatibility class II (MHC II)-dependent antigen presenting cells, and thereby reduce the immune activation. Alternatively, direct induction of immune mechanisms in vivo, such as B cell anergy in peripheral lymphoid tissues might account for this effect (49).

The cyclic peptide of the present invention comprises a peptide having an amino acid sequence of SEQ ID NO. 1. The number of amino acids and thus the length of the primary structure appears to be crucial for the biological effects of the various peptides of the present invention. A length of the cyclic peptide equal or above 24 amino acids (primary structure) is thought to be necessary and sufficient to obtain the reported results.

In accordance therewith, the invention relates to the general peptide structure as reflected by formula (I). It will also be understood by the ones skilled in the art that the individual amino acid may be replaced by another naturally occurring or synthetic amino acid, preferably if both amino acids belong to the same category of amino acids. In accordance therewith, for example, an acidic amino acid can be replaced by another acidic amino acid, a basic amino acid may be replaced by another basic amino acid and so on. It will also be acknowledged by the ones skilled in the art that one or several of the amino acids forming the peptide of the present invention may be modified. In accordance therewith any amino acid as used herein preferably also represents its modified form. For example, an alanine residue as used herein also comprises modified alanine. Such modifications may, among others, be a methylation or acylation or the like, whereby such modification or modified amino acid is preferably comprised by the present invention as long as the thus modified amino acid and more particularly the peptide containing said thus modified amino acid is still functionally active as defined herein, more particularly functionally active in accordance with the present invention. Respective assays for determining whether such a peptide, i. e. a peptide comprising one or several modified amino acids, fulfils this requirement, are known to the one skilled in the art and, among others, also described herein, particularly in the examples.

The invention comprises also derivatives of the peptides such as salts with physiologic organic and inorganic acids like HCl, H2SO4, H3PO4, malic acid, fumaric acid, citric acid, tartaric acid, acetic acid, and trifluoroacetic acid.

According to the practice in the art, sequences of peptides are indicated from the N-terminus to the C-terminus, whereby the N-terminus is at the left side and the C-terminus is at the right side of the respective depicted amino acid sequence. The peptides as described herein are cyclic peptides, which do not have termini, as these are covalently linked.

In a preferred embodiment the amino acids, e.g. for x(i), are selected from acidic, basic, neutral and/or aliphatic amino acids. Preferably an acidic amino acid is an amino acid selected from the group comprising Asp, Asn, Glu, and Gln; preferably a basic amino acid is an amino acid selected from the group comprising Arg and Lys; preferably a neutral amino acid is an amino acid selected from the group comprising Gly, Ala, Ser, Thr, Val, Leu, He; preferably an aliphatic amino acid is an amino acid which is selected from the group comprising Gly, Ala, Ser, Thr, Val, Leu, He, Asp, Asn, Glu, Gln, Arg, Lys, Cys and Met.

As used herein, the expression that one particular amino acid, such as, e. g., a basic amino acid, is replaced by a different amino acid which is selected from a respective particular group of amino acids, such as, e. g., the group comprising basic amino acids, preferably means that the particular amino acid is replaced by another, i.e. different amino acid under the proviso that such different amino acid is part of the respective particular group of amino acids.

The cyclic peptide (also referred to herein as "active compound") of the invention can be incorporated into pharmaceutical compositions suitable for administration. Such compositions typically comprise the cyclic peptide and a pharmaceutically acceptable carrier. As used herein the language "pharmaceutically acceptable carrier" includes solvents, dispersion media, coatings, antibacterial and antifungal agents, isotonic and absorption delaying agents, which are compatible with pharmaceutical administration. Additional active compounds may be incorporated into the compositions.

A pharmaceutical composition of the invention is formulated to be compatible with its intended route of administration. Preferable routes of administration include parenteral, e.g., intravenous or intraarterial administration. Solutions or suspensions used for parenteral: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyetheylene glycol), and mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is especially advantageous to formulate oral or parenteral compositions in dosage unit form for ease of administration and uniformity of dosage. Dosage unit form as used herein refers to physically discrete units suited as unitary dosages for the subject to be treated. Each unit contains a predetermined quantity of active compound calculated to produce the desired therapeutic effect in association with the required pharmaceutical carrier.

The active ingredient may be present in the pharmaceutical composition in the range of 1 μg/kg to 100 mg/kg, preferably 10 μg/kg to 1000 μg/kg, e.g. about 100 μg/kg, depending on the application form, preferably s.c. or i.v. application. A suitable dosing interval is from one week to three months, e.g. every two to four weeks.

It is within the present invention that the peptide and the pharmaceutical composition is used for the treatment of any of the diseases and patient groups as defined above including the treatment, amelioration or prevention of a disease caused by antibodies targeting the thyrotropin-TSH receptor (TSHR) in the thyroid gland in these patients by using the aforementioned compounds. Also, the peptides according to the present invention may be used for the preparation of a medicament for the treatment and/or prevention of any of the diseases and patient groups as defined above in connection with the pharmaceutical composition.

Finally, the present invention is related to a method for the treatment of patients as defined above, whereby the patient is in need of such treatment and whereby the method comprises administering to said patient a pharmaceutically effective amount of the peptide of the present invention, or the pharmaceutical composition or the medicament disclosed herein.

Preferably, a therapeutically effective dose refers to that amount of the active ingredient that produces amelioration of symptoms of a subject which can be determined by the one skilled in the art doing routine testing. A "patient" for the purposes of the present invention, i.e. to whom a compound according to the present invention or a pharmaceutical composition according to the present invention is administered, includes both humans and other animals and organisms. Thus the compounds, pharmaceutical compositions and methods are applicable to or in connection with both human therapy and veterinary applications, in the most preferred embodiment the patient is human.

LITERATURE

1. Weetman A P. Graves' disease. N Engl J Med 2000; 34:1236-1248
2. Ross D S. Radioiodine therapy for hyperthyroidism. N Engl J Med 2011; 364:542-550
3. Sundaresh V, Brito J P, Wang Z, Prokop L J, Stan M N, Murad M H, Bahn R S. Comparative effectiveness of therapies for Graves' hyperthyroidism: a systematic review and network meta analysis. J Clin Endocrinol Metab 2013; 98:3671-3677
4. Abraham-Nordling M, Törring O, Hamberger B, Lundell G, Tallstedt L, Calissendorf J, Wallin G. Graves' disease: a long-term quality of life follow up of patients randomized to treatment with antithyroid drugs, radioiodine or surgery. Thyroid 2005; 15:1279-1285
5. Bahn R S. Graves' ophthalmopathy. N Engl J Med 2010; 362:726-738
6. El Fassi D, Nielsen C H, Bonnema S, Hasselbalch H C, Hegedüs L. B lymphocyte depletion with the monoclonal antibody rituximab in Graves' disease: a controlled pilot study. J Clin Endocrinol Metabol 2007; 92:1769-1772

7. Heemstra K A, Toes R E, Sepers J, Pereira A, Corssmit E P, Huizinga T W J, Romijn J A, Smit J W. Rituximab in relapsing Graves' disease, a phase II study. Eur J Endocrinol 2008; 159: 609-615
8. Salvi M, Vannucchi G, Curro N, Campi I, Covelli D, Dazzi D, Simonetta S, Guastella C, Pignataro L, Avignone S, Beck-Peccoz P. Efficacy of B cell targeted therapy with rituximab in patients with active moderate—severe Graves' oritopathy: a randiomized controlled study. J Clin Endocrinol Metab 2015; 100: 422-431
9. Stan M N, Garrity J A, Carranza Leon B G, Prabin T, Bradley E A, Bahn R S. Randomized Controlled Trial of Rituximab in Patients With Graves' Orbitopathy. J Clin Endocrinol Metabol 2015; 100:432-441
10. Larche M, Wraith D C. Peptide-based therapeutic vaccines for allergic and autoimmune diseases. Nature Med 2005; 11(4):569-576
11. Soyka M, van de Veen W, Holzmann D, Akdis M, Akdis C A. Scientific foundations of allergen-specific immunotherapy for allergic diseases. Chest 2014; 146:1347-1357
12. Valenta R, Ferreira F, Focke-Tejkl M, Linhart B, Niederberger V, Swoboda I, Vrtala S. From allergen genes to allergy vaccines. Ann Rev Immunol 2010; 28:211-241
13. Marth K, Focke-Tejkl M, Lupinek C, Valenta R, Niederberger V. Allergen Peptides, Recombinant Allergens and Hypoallergens for Allergen-Specific Immunotherapy. Curr Treatment Options in Allergy 2014; 1:91-106
14. Jahns R, Boivin V, Hein L, Triebel S, Angermann C E, Ertl G, Lohse M J. Direct evidence for a β1-adrenergic receptor directed autoimmune attack as a cause of idiopathic dilated cardiomyopathy. J Clin Invest 2004; 113: 1419-1429.
15. Freedman N J, Lefkowitz R J. Anti-β1-adrenergic receptor antibodies and heart failure: causation, not just correlation. J Clin Invest 2004; 113:1379-1382
16. Boivin V, Beyersdorf N, Palm D, Nikolaev V O, Schlipp A, Willer J, Schmidt D, Kokoski V, Kerkau T, Hünig T, Ertl G, Lohse M J, Jahns R. Novel receptor-derived cyclopeptides to treat heart failure caused by anti-β1-adrenoceptor antibodies in a human-analogous rat model. PlosOne 2015; 10(2) e0117589 (doi 10.1371/journal-.pone.0117589)
17. Münch G, Boivin-Jahns V, Holthoff H P, Adler K, Lappo M, Truöl S, Degen H, Steiger N, Lohse M J, Jahns R, Ungerer M. Administration of the cyclic peptide COR-1 (phase I study): ex vivo measurements of anti-β1 receptor antibody neutralization and of immune parameters. Eur J Heart Failure 2012; 14:1230-1239
18. Störk S, Plotnikov A N, Peters G, Davies B E, Nnane I, Rivas D, Tesfaye F, Kääb S, Bauer A, Luchner A, Ungerer M, Jahns R, Lohse M J, Ertl G. Effects of JNJ-54452840, an Anti-β1 Receptor Antibody Cyclopeptide in Heart Failure Patients: A Randomized, Double-blind, Parallel-group, Phase-2 Pilot Study. Cardiovac Pharmacol 2016, 5:4; DOI: 10.4172/2329-6607.1000190
19. Nagayama Y, Kita-Furuyama M, Ando T, Nakao K, Mizuiguchi H, Hayakawa T, Eguchi K, Niwa M. A novel murine model of Graves' hyperthyroidism with intramuscular injection of adenovirus expressing the thyrotropin receptor. J Immunol 2002; 168:2789-2794
20. Chen C R, Pichurin P, Nagayama Y, Latrofa F, McLachlan S M, Rapoport B. The thyrotropin receptor autoantigen in Graves disease is the culprit as well as the victim. J Clin Invest 2003; 111:1897-1904
21. Gilbert J A, Kalled S L, Moorhead J, Hess D M, Rennert P, Li Z, Khan M Z, Banga J P. Treatment of autoimmune hyperthyroidism in a murine model of Graves' disease with TNF family ligand inhibitors suggests a key role for B cell activating factor in disease pathology. Endocrinology 2006; 147:4561-4568
22. Holthoff H P, Göbel S, Li Z M, Fassbender J, Reimann A, Zeibig S, Lohse M J, Münch G, Ungerer M. Prolonged TSH receptor A subunit immunization of female mice leads to a long-term model of Graves' disease, tachycardia and cardiac hypertrophy. Endocrinology 2015; 156: 1577-1589.
23. Ungerer M, Fassbender J, Li Z, Münch G, Holthoff H P. Review of mouse models of Graves' disease and orbitopathy—novel treatment by induction of tolerance. Clin Rev Allerg Immunol 2016, open access online publication 2 Jul. 2016; doi: 10.1007/s12016-016-8562-7
24. Parmentier M, Libert F, Maenhaut C, Lefort Gerard C, Peret J, Van Sande J, Dumont J E, Vassart G. Molecular cloning of the thyrotropin receptor. Science 1989; 246: 1620-1622
25. Nagayama Y, Kaufman K D, Seto P, Rapoport B. Molecular cloning, sequence and functional expression of the cDNA for the human thyrotropin receptor: Biochem Biophys Res Commun 1989; 165: 1184-1190
26. Dahab G M, Kheriza M M, EL-Beltagi H M, Fouda A M M, Sharaf El-Din O A. Digital quantification of fibrosis in liver biopsy sections: Description of a new method by Photoshop software. J Gastroenterol Hepatol 2004; 19: 78-85
27. McLachlan S M, Nagayama Y, Rapoport B. Insight into Graves' hyperthyroidism from animal models. Endocrine Reviews 2005; 26:800-832
28. Nagayama Y. Graves' animal models of Graves' hyperthyroidism. Thyroid 2007; 17: 981-988
29. Kaneda T, Honda A, Hakozaki A, Fuse T, Muto A, Yoshida T. An improved Graves' disease model established by using in vivo electroporation exhibited long-term immunity to hyperthyroidism in BALB/c mice. Endocrinology 2007; 148:2335-2344
30. Arima T, Shimojo N, Yamaguchi K I, Tomiita M, Kohn L D, Kohnoi Y.
Enhancement of experimental Graves' disease by intranasal administration of a T cell epitope of the thyrotropin receptor. Clin Immunol 2007; 127: 7-13
31. Misharin A V, Nagayama Y, Aliesky H A, Mituzori Y, Rapoport B, McLachlan S M. Attenuation of induced hyperthyroidism in mice by pretreatment with thyrotropin receptor protein: deviation of thyroid-stimulating to non-functional antibodies. Endocrinology 2009; 150:3944-3952
32. Wu L P, Xun L, Yang J, Tian Z, Gao S, Zhang Y, Hou P, Shi B. Induction of murine neonatal tolerance against Graves' disease using recombinant adenovirus expressing the TSH receptor A subunit. Endocrinology 2011; 152: 1165-1171
33. Ueki I, Abiru N, Kobayashi M, Nakahara M, Ichikawa T, Eguchi K, Nagayama Y. B cell targeted therapy with anti-CD20 monoclonal antibody in a mouse model of Graves' hyperthyroidism. J Translat Immunology 2011; 163:309-317
34. Furmaniak J, Sanders J, Nunez Miguel R, Rees Smith B. Mechanism of action of TSHR autoantibodies. Horm Metab Res 2015; 47:735-752
35. Neumann S, Eliseeva E, McCoy J, Napolitano G, Giuliani C, Monaco F, Huang W, Gershengorn M C. A new small molecule antagonist inhibits Graves' disease antibody activation of the TSH receptor. J Clin Endocrin Metabol 2011; 96:548-554

36. van Zeijl C J J J, van Koppen C J, Surotseva O, de Gooyer M E, Plate R, Conti P, Karstens W J, Timmers M, Saeed P, Wiersinga W M, Miltenburg A M M, Fliers E, Boelen A. Complete inhibition of rhTSH-, Graves' disease IgG- and M22-induced cAMP production in differentiated orbital fibroblasts by a low molecular weight TSHR antagonist. J Clin Endocrinol Metabol 2012; 97: E781-E785
37. Neumann S, Place R F, Krieger C C, Gershengorn M C. Future prospects for the treatment of Graves' hyperthyroidism and eye disease. Horm Metab Res 2015; 47:789-796
38. Creticos P S. Advances in synthetic peptide immunoregulatory epitopes. World Allergy Org J 2014; 7:30
39. Jutel M, Akdis C A. Immunological mechanisms of allergen-specific immunotherapy. Allergy 2011; 66: 725-32
40. Murphy K, Travers P, Walport M. Janeways's immunobiology. Garland Science Editors, New York 2008; ISBN 0-8153-4123-7, pages 347-348
41. Holthoff H P, Zeibig S, Boivin V, Bauer J, Lohse M J, Kääb S, Clauss S, Jahns R, Schlipp A, Münch G, Ungerer M. Detection of Anti β1-AR Auto-Antibodies in Heart Failure by a Cell-Based Competition ELISA. Circulation Research 2012; 111: 675-684
42. Kamijo K, Ishikawa K, Tanaka M. Clinical evaluation of 3rd generation assay for thyrotropin receptor antibodies: the M22-biotin-based ELISA initiated by Smith. Endocrine J 2005; 52:525-529
43. Tozzoli R, Bagnasco M, Giavarina D, Bizzaro N. TSH receptor autoantibody immunoassay in patients with Graves' disease: improvement of diagnostic accuracy over different generations and methods. Systematic review and meta-analysis. Autoimmun Rev 2012; 12:107-113
44. Zhao S X, Tsui S, Cheung A, Douglas R S, Smith T J, Banga J P. Orbital fibrosis in a mouse model of Graves' disease induced by genetic immunization of thyrotropin receptor cDNA. J Endocrinol 2011; 210:369-377
45. Moshkelgosha S, So P W, Deasy N, Diaz-Cano S, Banga J P. Retrobulbar inflammation, adipogenesis, and acute orbital congestion in a preclinical female mouse model of Graves' orbitopathy induced by thyrotropin receptor plasmid in vivo electroporation. Endocrinology 2013; 154: 3008-3015
46. Banga J P, Moshkelgosha S, Berchner-Pfannschmidt U, Eckstein A. Modelling Graves' orbitopathy in experimental Graves' disease. Horm Metab Res 2015; 47:797-803
47. Klein I, Ojamaa K. Thyroid hormone and the cardiovascular system. New Engl J Med 2001; 344:501-509
48. von Olshausen K, Bischoff S, Kahaly G, Mohr-Kahaly S, Erbel R, Beyer J, Meyer J. Cardiac arrhythmias and heart rate in hyperthyroidism. Am J Cardiol 1989; 63: 930-933
49. Blank M, Shoenfeld Y. B cell targeted therapy in autoimmunity. J Autoimmunity 2007; 28:62-68

The present invention will now be further illustrated by the following figures and examples.

FIG. 1A shows the time course of immunizations, administrations of therapeutic peptides and measurements. At 0 weeks immunisations started, at 11 weeks treatments started. "- -►" (filled arrow) indicates i.m. immunisations/ECG to measure heart rates; "→" (open arrow) indicates i.v. administrations of peptides/vehicle (NaCl); * indicates blood withdrawals; ° indicates determination of T4 and/or anti-TSHR antibodies from serum samples; # indicates final ECG recordings/Thyroid and orbital histopathology.

FIG. 1B shows a schematic structure of the thyroid stimulating hormone (TSH) receptor. The cyclic peptides in accordance with the invention were derived from the eighth loop structure of the leucine-rich repeat domain of the extracellular A subunit of the TSHR, as marked in darker colour.

Figure 2:
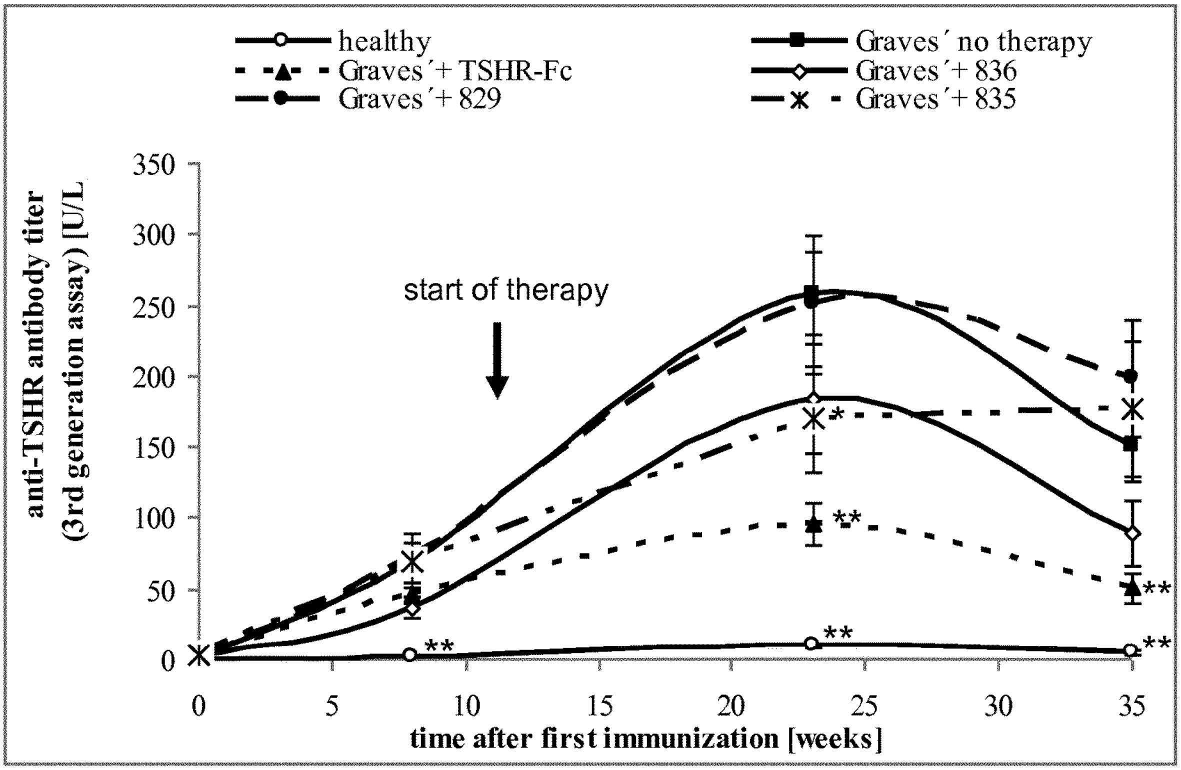
FIG. 2 shows the effect of peptide of the present invention on time course of anti-TSHR titers. The peptide in accordance with the present invention is indicated as "836".

FIG. 2 shows the effect of peptide therapy on time course of anti-TSHR titers, as measured by $3^{rd}$ generation ELISA, in which serum samples are used to determine inhibition of M22-binding to coated plates. The measurements were carried out in Ad-TSHR-immunized mice treated by either 4-weekly injections with vehicle (0.9% NaCl, "Graves' no therapy", n=25 mice), or administrations of 1 mg/kg body weight of peptide of the invention 836 (12 mice), or of peptide 829 (13 mice), or of TSHR-Fc (18 mice), or of control peptide 835 (13 mice). In addition, age-matched immunologically naïve unimmunized mice ("healthy", 19 animals) were investigated. Data are represented as mean±SEM. Significance over time was tested by analysis of variance (ANOVA) of groups at given time points, and controlled by ANOVA for repeated measurements within one group, followed by LSD post-hoc testing. *$p<0.05$, and **$p<0.005$, compared to the TSHR-immunized group treated with only NaCl ("Graves' no therapy").

Figure 3:
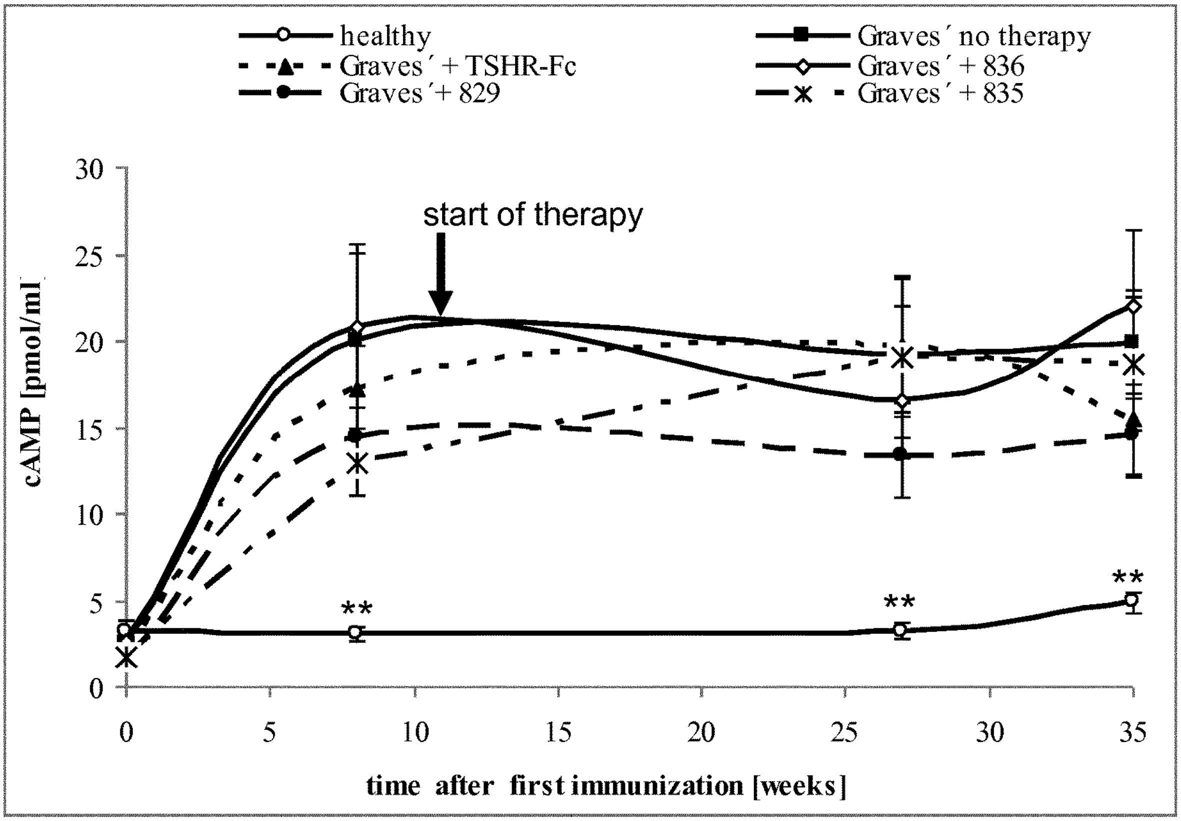
FIG. 3 shows the effect of the peptide of the present invention on cAMP stimulation in TSHR-expressing test cells, as determined in sera taken from the mice during the experiment.

FIG. 3 shows the effects of peptide therapy on the capacity of anti-TSHR antibodies to stimulate cAMP generation in CHO cells expressing the human TSHR. The measurements were carried out in Ad-TSHR-immunized mice treated by either 4-weekly injections with vehicle (0.9% NaCl, "Graves' no therapy", n=25 mice), or administrations of 1 mg/kg body weight of peptide of the invention 836 (12 mice), or of peptide 829 (13 mice), or TSHR-Fc (18 mice), or of control peptide 835 (13 mice). In addition, age-matched immunologically naïve unimmunized mice ("healthy", 19 animals) were investigated. Data are represented as mean±SEM. Differences between groups were tested by AVOVA followed by post hoc LSD testing.**$p<0.005$ compared to the TSHR-immunized group treated with only NaCl ("Graves' no therapy").

Figure 4:
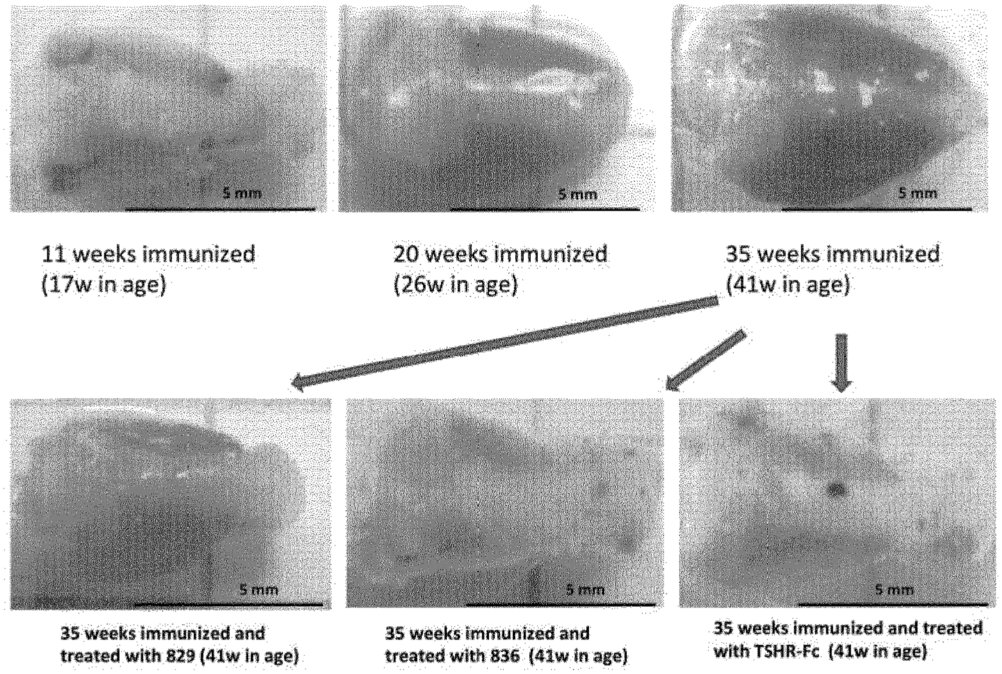
FIG. 4 shows the effect of the peptide of the present invention on thyroid size.
Figure 4:
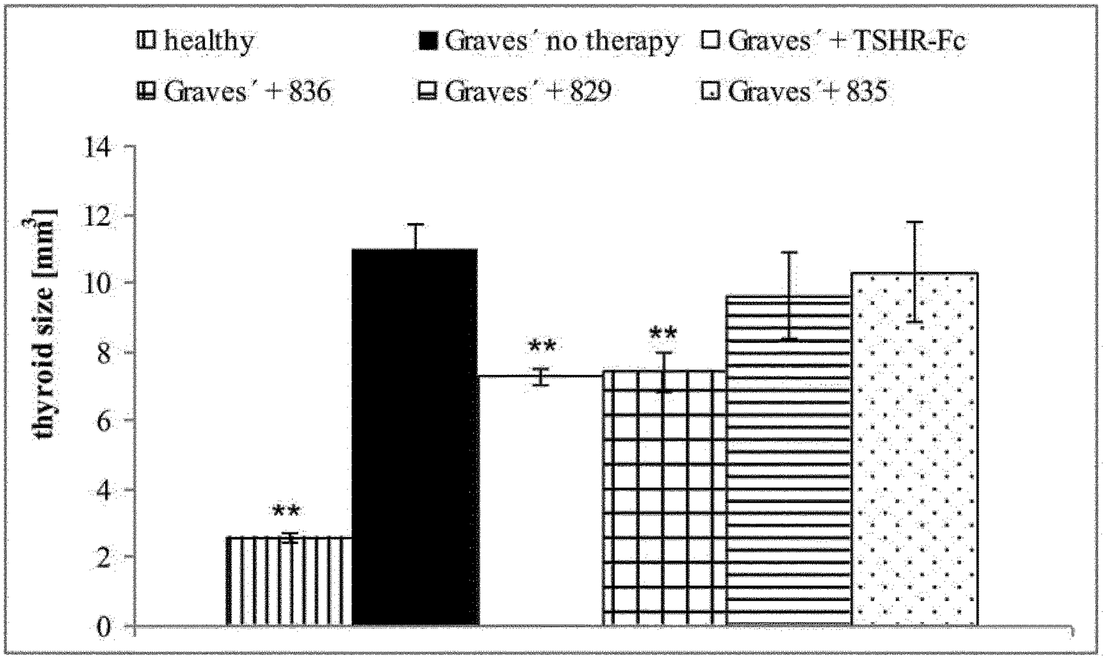

FIG. 4 shows the effect of the peptide of the invention on thyroid size. FIG. 4A shows a comparison of thyroids of mice immunized with Ad-THSR, treated with vehicle NaCl only and sacrificed at various time stages (upper panel) with a thyroid from a 35 week-old TSHR-immunized mouse treated with TSHR-Fc, or peptide of the invention 836 or comparison peptide 829 (lower panels). Representative images are shown. In FIG. 4B, the effects of peptide therapy on thyroid sizes were investigated at the end of the experiment. The measurements were carried out in Ad-TSHR-immunized mice treated by either 4-weekly injections with vehicle (0.9% NaCl, "Graves' no therapy", n=25 mice), or administrations of 1 mg/kg body weight of peptide of the invention 836 (12 mice), or of peptide 829 (13 mice), or of TSHR-Fc (18 mice), or of control peptide 835 (13 mice). In addition, age-matched immunologically naïve unimmunized mice ("healthy", 19 animals) were investigated. The mean thyroid sizes in $mm^3$ are shown with SEM. Differences between groups were tested by AVOVA followed by post hoc LSD testing. ** indicates statistical significance ($p<0.001$) compared to the TSHR-immunized group treated with only NaCl ("Graves' no therapy").

Figure 5:
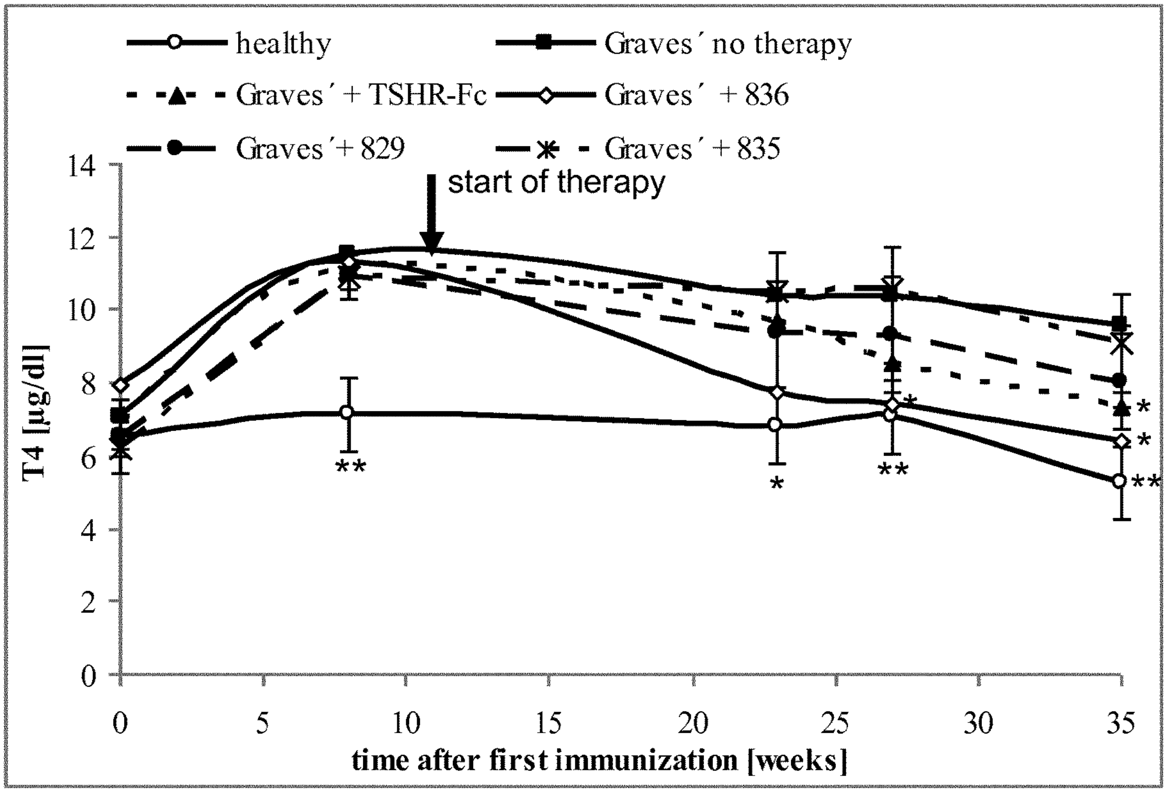
FIG. 5 shows the effect of the peptide of the present invention on serum thyroxin (T4) levels.

In FIG. 5 the effects of peptide therapy on serum thyroxin levels were evaluated. The measurements were carried out in Ad-TSHR-immunized mice treated by either 4-weekly injections with vehicle (0.9% NaCl, "Graves' no therapy", n=25 mice), or administrations of 1 mg/kg body weight of peptide of the invention 836 (12 mice), or of peptide 829 (13 mice), or TSHR-Fc (18 mice), or of control peptide 835 (13 mice). In addition, age-matched immunologically naïve unimmunized mice ("healthy", 19 animals) were investigated. Data are represented as means±SEM. Significance over time was tested by analysis of variance (ANOVA) of groups at given time points, and controlled by ANOVA for repeated measurements within one group, followed by LSD post-hoc testing. *p<0.05, and **p<0.005, compared to the TSHR-immunized group treated with only NaCl ("Graves' no therapy").

Figure 6:
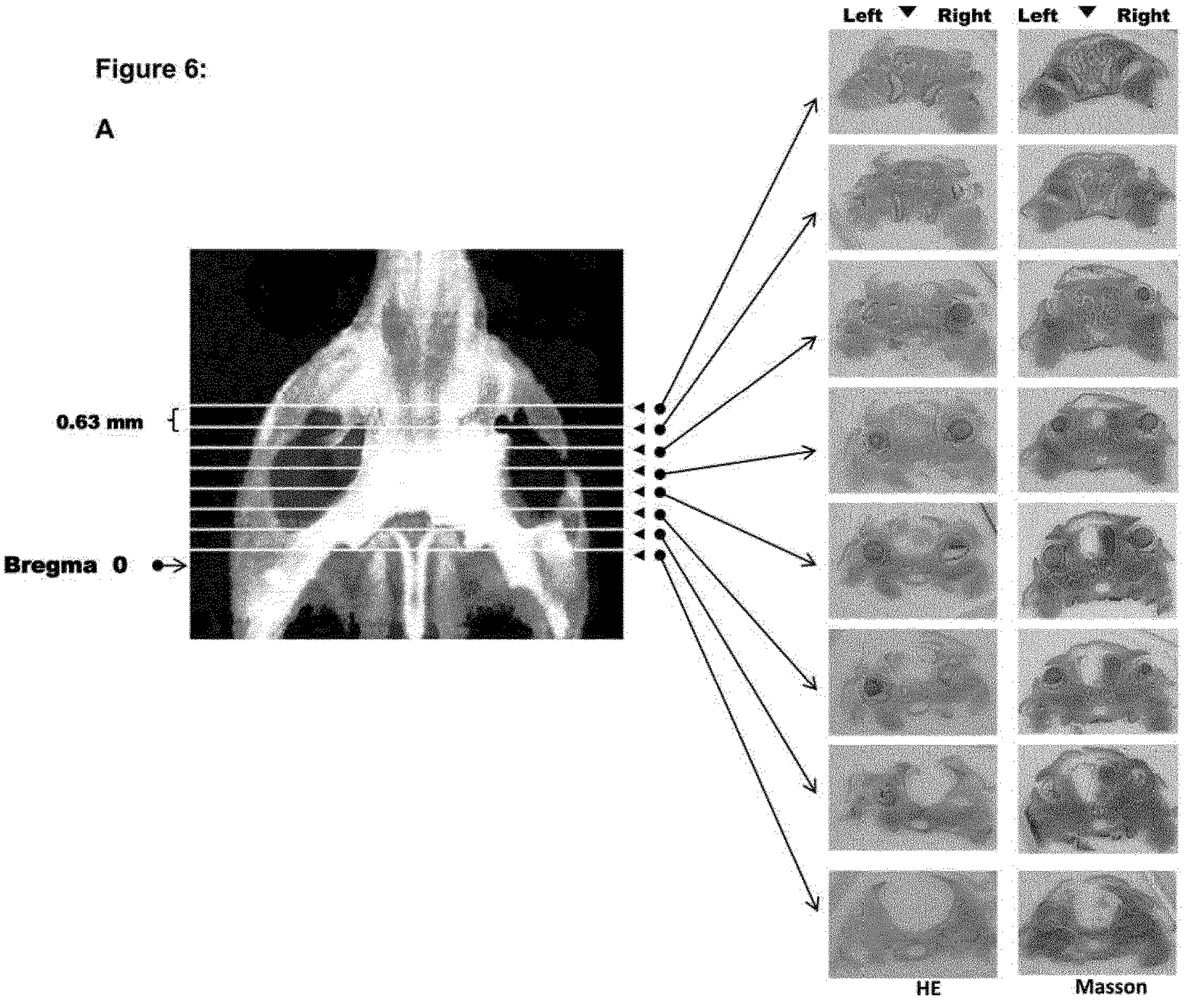
FIG. 6 shows a histological investigation of orbital sections.
Figure 6:
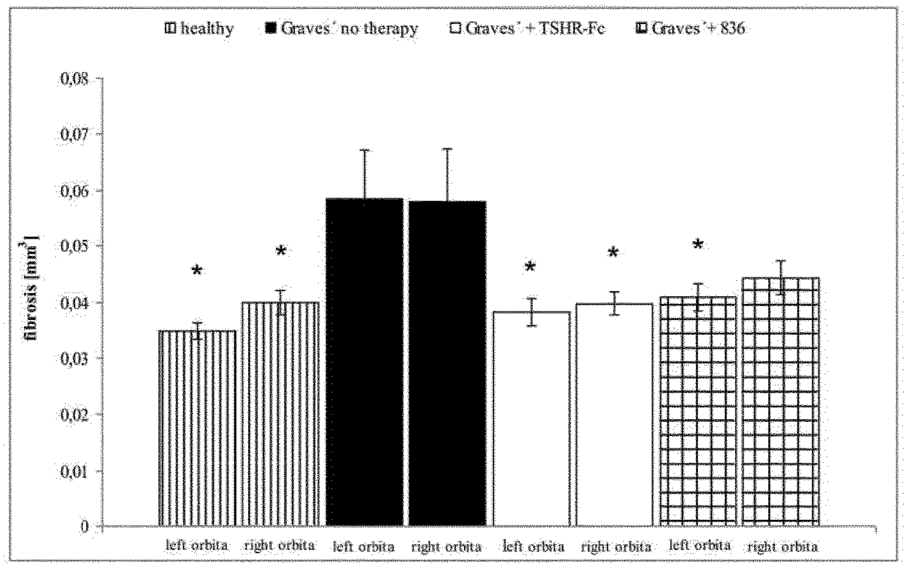

FIG. 6 summarizes the results of histological investigation of orbital sections. FIG. 6A shows representative images of coronary sections of a mouse orbita and neighbouring tissues. The sections were taken at defined distances from the mouse bregma. Interstitial connective tissue was then stained in green (Masson's trichrome stain). For clarity, both HE stained sections (left panels) and Masson's stained sections (right panels) are shown next to each other. FIG. 6B: the effects of peptide therapy on severity of retro-orbital fibrosis were evaluated in histological sections of all available animals. The measurements were carried out in Ad-TSHR-immunized mice treated by either 4-weekly injections with vehicle (0.9% NaCl, "Graves' no therapy", n=9 mice), or administrations of 1 mg/kg body weight of peptide 836 (11 mice) or TSHR-Fc (11 mice). In addition, age-matched immunologically naïve unimmunized mice ("healthy", 10 animals) were investigated. The mean total fibrosis volumes of each right and left orbita, as assessed by digitized image analysis of all sections, and consecutive integrations, are shown with SEM. Differences between groups were tested by ANOVA, *p<0.05 compared to the TSHR-immunized group treated with only NaCl ("Graves' no therapy").

Figure 7:
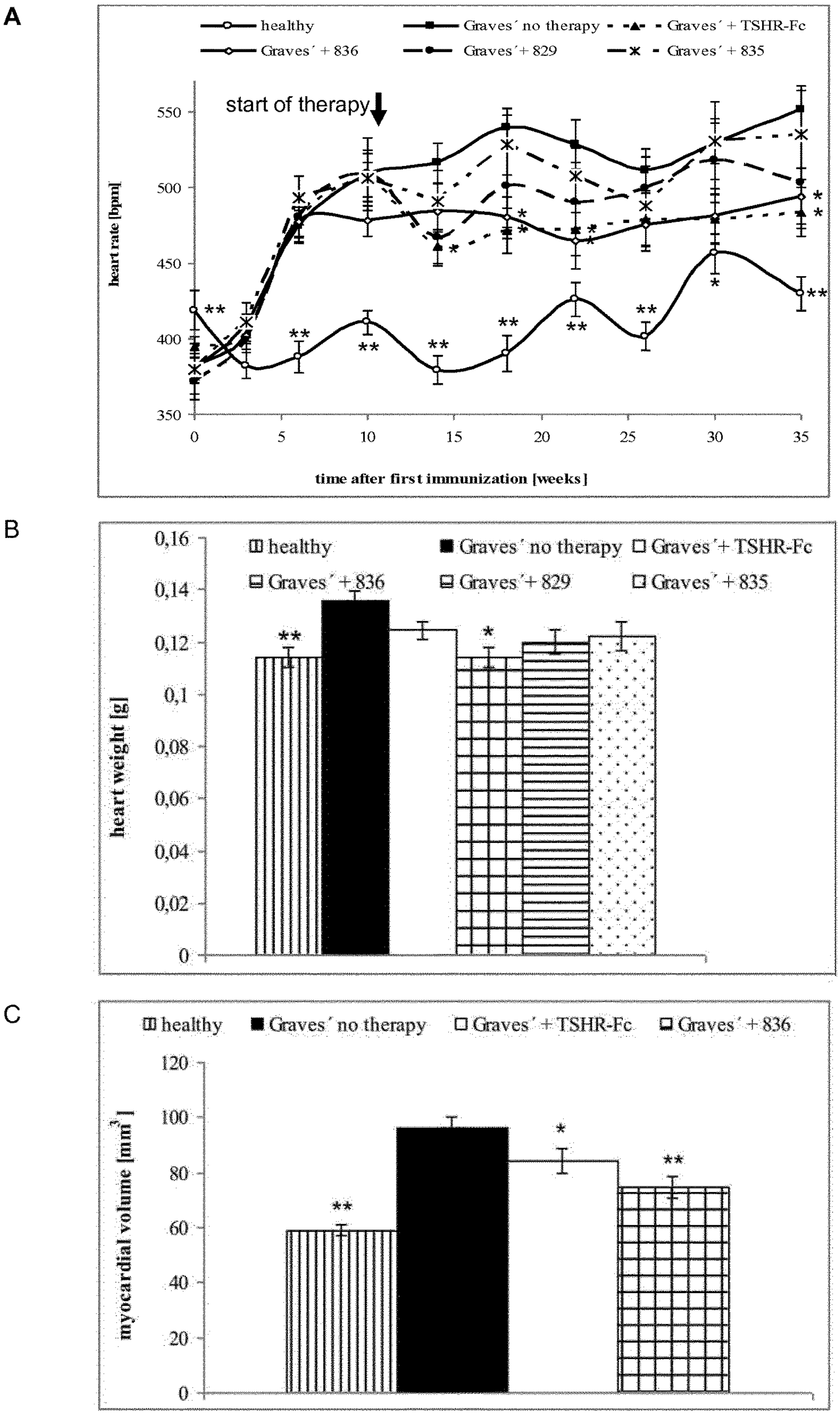
FIG. 7 shows the effect of the peptide of the present invention on heart rates (FIG. 7A), heart weights (FIG. 7B) and ventricular volumes (FIG. 7C).

In FIG. 7 the effect of the peptide therapy on heart rates at various times during the experiment (A), and on heart weights (B) and cardiac ventricular volumes (C) at the end of the experiment were evaluated in all animals. The measurements were carried out in Ad-TSHR-immunized mice treated by either 4-weekly injections with vehicle (0.9% NaCl, "Graves' no therapy", n=25 mice), or administrations of 1 mg/kg body weight of peptide of the invention 836 (12 mice), or of peptide 829 (13 mice), or TSHR-Fc (18 mice). In addition, age-matched immunologically naïve unimmunized mice ("healthy", 19 animals) were investigated. Data are represented as mean±SEM. Significance over time was tested by analysis of variance (ANOVA) of groups at given time points, and controlled by ANOVA for repeated measurements within one group, followed by LSD post-hoc testing. *p<0.05, and **p<0.005, compared to the TSHR-immunized group treated with only NaCl ("Graves' no therapy").

Figure 8:
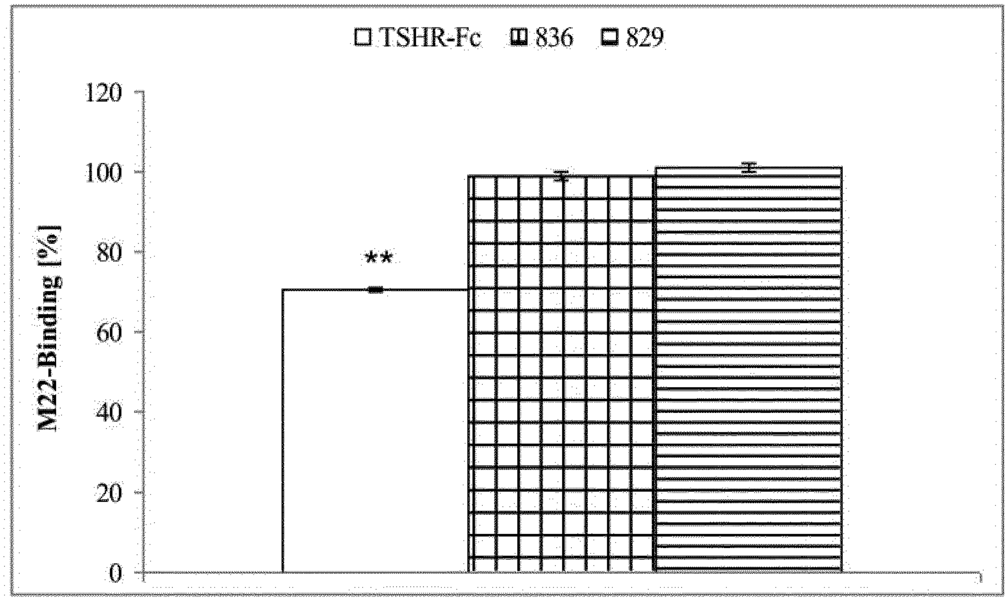
FIG. 8 shows the effect of the peptide of the present invention on anti-TSHR antibody titers (FIG. 8A) and on cAMP stimulation in TSHR-expressing test cells (FIG. 8B) ex vivo (anti-TSHR-antibody positive serum samples).
Figure 8:
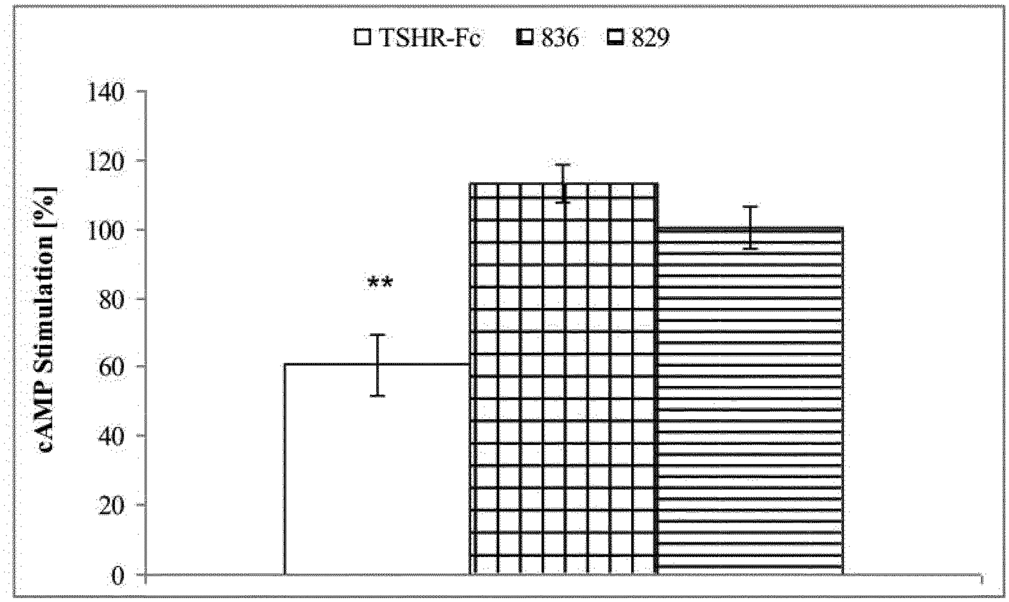

In FIG. 8 the effects of peptides on anti-TSHR antibody titers (A) and on cAMP stimulation in TSHR-expressing test cells (B) were studied ex vivo (anti-TSHR-antibody positive serum samples). Each measurement was carried out in 4 samples. Results are shown as % of untreated controls with standard errors of the means (SEM). Significance was tested by analysis of variance (ANOVA) between groups, followed by LSD post-hoc testing. **p<0.001, compared to controls

EXAMPLES

Materials and Methods

Recombinant Adenovirus

The DNA sequence coding for the first 289 amino acids of the human TSH-receptor (23, 24) was cloned into the Microbix Admax™ adenovirus expression system as described before (22). HEK293A cells were used to propagate until first viral plaques became visible. This system results in recombinant replication-deficient E1 and E3-deficient adenovirus type 5. A control adenovirus containing only the reporter gene GFP (Ad-GFP) was amplified and purified in the same manner.

Synthesis of Cyclic Peptides

Cyclic peptides with structural homology to the 10 cylindrical loops of the TSHR leucine rich domain were designed as outlined in Table 1.

TABLE 1

TSHR-Peptides, Head To Tail Cyclization

| Peptide # | (derived from TSHR sequence aa): | |
|---|---|---|
| 829 | 26-49 | SPPCECHQEEDFRVTCKDIQRIPS (SEQ ID NO: 2) |
| 830 | 50-73 | LPPSTQTLKLIETHLRTIPSHAFS (SEQ ID NO: 3) |
| 831 | 73-89 | SNLPNISRIYVSIDVTL (SEQ ID NO: 4) |
| 832 | 98-121 | YNLSKVTHIEIRNTRNLTYIDPDA (SEQ ID NO: 5) |
| 833 | 122-145 | LKELPLLKFLGIFNTGLKMFPDLT (SEQ ID NO: 6) |
| 834 | 146-163 | KVYSTDIFFILEITDNP (SEQ ID NO: 7) |
| 835 | 170-193 | NAFQGLCNETLTLKLYNNGFTSVQ (SEQ ID NO: 8) |
| 836 | 194-217 | GYAFNGTKLDAVYLNKNKYLTVID (SEQ ID NO: 1) |
| 837 | 218-237 | KDAFGGVYSGPSLLDVSQTS (SEQ ID NO: 9) |
| 838 | 242-265: | PSKGLEHLKELIARNTWTLKKLPL (SEQ ID NO: 10) |

Table 1: Amino acid sequences derived from human TSHR which were used to create cyclic peptides which were used in the study. After synthesis, each peptide was cyclized head-to-tail. Each peptide approximates one of the ten loops of the leucine rich region of TSHR domain A. In accordance with the amino acid length of these loops, 24-meric peptides were used with the exception of peptides derived from the $3^{rd}$, $6^{th}$ and $9^{th}$ loop. For technical reasons, cyclic 24-mer could not be provided for these loops, so that 17-meric ($3^{rd}$ and $6^{th}$ loop) or 20-meric ($9^{th}$ loop) peptides were used instead.

Specifically, the sequence of peptide 836 (peptide of the present invention) replicates the eighth cylindrical loop, whereas peptide 829 was designed in analogy to the first loop of the TSHR LRR. In view of its biological inactivity, peptide 835 is shown as an additional inactive control cyclic peptide. They were synthesized by Biosyntan Berlin according to described protocols of fluorenylmethoxycarbonyl (FMOC) resin-based amino acid chain elongation, and subsequent head-to-tail cyclisation. Fmoc amino acid or Fmoc dipeptide was attached to the 2-Chlorotrityl chloride resin (RAPP Polymere GmbH, Germany) yielding a loading of 0.30 mmol/g resin. Peptide synthesis was done by a standard cycle of deblocking with 30% piperidine/N,N-dimethylformamide (DMF, 5+12 min) and coupling with 3 eq. Fmoc-amino acid/O-(7-Azabenzotriazol-1-yl)-N,N,N',N'-tetramethyluronium-hexafluorphosphate (HATU)/6 eq. N-methylmorpholine (NMM) in DMF (double coupling, 2×30 min). After cleavage from the resin by 20% hexafluoroisopropanol (HFIP)/DCM (2×20 min) the isolated crude peptide was cyclized by 1.5 eq 7-(Azabenzotriazol-1-yloxy) tripyrrolidinophosphonium hexafluorophosphate (PyAOP)/3 eq diisopropylethylamine (DIEA) in DMF over night, the solvent evaporated and the crude peptide deblocked by trifluoroacetic acid (TFA)/water/thioanisol (TIS) (95:5:3) during 2 h. Then, the peptides were purified up to 95% by means of HPLC and analyzed by MALDI-TOF mass spectrometry. This quality control reconfirmed that amino acids had been correctly included into the peptides, and their cyclisation was evident from the experimental determination versus theoretical prediction of molecular weights: As examples, values of observed versus predicted molecular weight were 2703.2 vs. 2703.2 for peptide 836, 2800.0 vs 2800.0 for peptide 829, and 2657.0 vs. 2657.1 for control peptide 835.

Expression and Purification of TSHR Fusion Protein

The fusion protein consists of the first 289 amino acids of the human TSH receptor (extracellular TSHR A-subunit) followed by a GGR linker and the Fc portion of human IgG2. The cDNA sequence adapted for hamster codon usage was produced synthetically and cloned into the plasmid vector pcDNA5/FRT. This expression vector was transfected into CHO Flp-In cells together with the plasmid pOG44, providing site-directed recombination. After selection of a stably expressing clone, the fusion protein was purified from suspension culture supernatant by ProteinG chromatography and dialysed against PBS.

Studies in Immunized Mice

Female BALB/c mice were delivered from Charles River, Sulzfeld, Germany, and were adapted for at least one week to start experiments at the age of 6 weeks. Animals were kept under standard housing conditions (23±2° C., 55±10% RH) in groups of ten animals in GR1800DD cages (Tecniplast®). All animal experiments were approved by the local animal welfare authority and Ethics committee at the Regierung von Oberbayern (Government of Upper Bavaria) in Munich, Germany (no. 55.2-1-54-2531-25-12), and carried out in accordance to the World Medical Association (Declaration of Helsinki), and the European Commission guidelines (Directive 2010/63/EU). All guidelines for care of animals were respected. Mice received $10^{10}$ plaque-forming units (pfu) of adenovirus carrying the A-subunit of the TSHR gene. In addition, age-matched immunologically naïve mice were studied for comparison. For immunisation, mice were anaesthetized with isoflurane (introduction 5%, maintenance 1.5-2%) and placed on a heating pad. The adenovirus was injected into the left and right femoral muscles in a volume of 25 µl each. For blood withdrawal, mice were placed under infrared light for at least 30 minutes for dilatation of the tail veins, then moved to a restrainer. 100 µl of blood was withdrawn out of the left or right tail vein with a 27G needle. Blood was centrifuged at 2400 g for 15 minutes at room temperature and serum was stored at −20° C. At the end of the study (before euthanasia), blood was withdrawn intracardiacally in deep anesthesia (170 mg/kg ketamine+17 mg/kg xylazine) with a 1 ml syringe and a 24G needle and treated as mentioned above.

The study protocol used three 3-weekly immunizations ("initiation") and followed by a "maintenance" phase with further regular 4-weekly boosts until the 9th immunisation, as described before (22). Mice were randomly assigned to therapeutic groups. Therapy (either 1 mg/kg body weight peptides or 0.9% NaCl vehicle control) was given 1 week after the 4th immunization by IV injection into a tail vein, and then continued at 4-weekly intervals, as described before for the treatment of anti-β1AR (16). The fusion protein TSHR-Fc was given IV at identical times at doses of 1 mg/kg, but had to be applied together with the histamine receptor blocker clemastin (Tavegil®) at a dose of 0.02 mg per mouse (25 g body weight) to avoid clinical symptoms of allergic reaction, which had been observed in initial pilot studies of TSHR-Fc administration in mice. A detailed immunisation schedule is shown in FIG. 1A.

When mice were subjected to anaesthesia for immunisation, their heart function was monitored with an electrocardiogram (ECG amplifier module, Harvard Apparatus, Hugo Sachs electronics) and recorded with a special software, which allows to determine the heart rate from the ECG reading (Haemodyn, Hugo Sachs electronics). ECG was also performed in anaesthesia before animals were euthanized for histological exam at the end of the study.

Studies in Native Mice

BALB/c mice were adapted for at least one week to start experiments at the age of 12 weeks. Animals were kept as described before. This study was approved by the local animal welfare authority and Ethics committee at the Regierung von Oberbayern (Government of Upper Bavaria) in Munich, Germany (no. 55.2-1-54-2532.0-32-15), and carried out in accordance to the European Commission guidelines. Peptides (either 1 mg/kg body weight or NaCl vehicle control) were given by IV injection into a tail vein of these naïve mice (n=5 per group), and then continued at 4-weekly intervals for 6 months, as described before for the therapeutic study in immunized mice. Serum samples were taken at identical intervals.

Measurements in Mouse Sera

Anti-TSHR autoantibody titers and potency of antibodies to stimulate TSHR-dependent cAMP levels in test cells were determined before start of immunisation (basal value), 56 days after first immunisation, 133 days after first immunisation, and 189 days after first immunisation, and at the end of experiment. To this aim, 2 different assays were used:

1) "3$^{rd}$ generation assay": Antibodies against TSHR were detected by a commercially available 3rd generation enzyme immunoassay provided by RSR Limited, Avenue Park, Pentwyn, Cardiff, U.K., in which the of the human Graves patient-derived M22 monoclonal antibody and serum antibodies compete for binding sites on immobilized TSHR. The assay is also used in Roche's Cobas® assay (04388790) for ECLIA with minor modifications. The assay was performed using 30 µl 1:10 (PBS) diluted serum in at least double determination according to the manufacturer's instructions.

2) Thyroid stimulating antibodies in the serum of hyperthyroid mice were analysed by measuring cyclic adenosine monophosphate (cAMP) generation in Chinese hamster ovary (CHO) cells JP2626 expressing the human TSHR (kindly provided by Dr. Gilbert Vassart, Brussels, Belgium). CHO cells were seeded into 96-well plates (30000 cells per well) and incubated for 24 hours in Dulbecco's modified Eagle medium (DMEM, Invitrogen Ltd) containing 2% fetal calf serum. Then, DMEM was removed and mice serum was diluted 1:8 in 40 µl HBSS buffer (20 mM Hepes, 1.26 mM $CaCl_2$), 5.33 mM KCl, 0.44 mM $KH_2PO_4$, 0.5 mM $MgCl_2$, 0.4 mM $MgSO_4$, 4.2 mM $NaHCO_3$, 5.6 mM glucose, and 222 mM Sucrose, pH7.2) supplemented with 1.5% BSA and 0.5 mM isobutyl-1-methylxanthine (Sigma-Aldrich, Pole, UK) and added to each well. After incubation for 2.5 hours at 37° C. the cAMP release in the medium was measured in duplicates by a competitive immunoassay ELISA (#EMSCAMPL, Thermo Fisher Scientific, Waltham, Mass., USA).

Total thyroxine (T4) was measured by immunoassay kit (#T4044T-100, Calbiotech Inc, Austin, Calif.) in duplicate determination.

Histological Analysis

After euthanasia, dissection of the thyroid glands was performed under a stereomicroscope, as described before (22). Briefly, cross cuts at the level above the larynx and below the seventh cartilage ring were made and the glands with the tracheae and oesophagi were removed from the necks. Tissue blocks were kept in 4% neutral para-formaldehyde (PFA), washed in PBS 3 times and embedded in optimum cutting temperature (OCT) formulation (Tissue-Tek® O.C.T.™ compound, VWR Chemicals, Leuven, Belgium). Consecutive 5 μm-thick cross sections were cut at a fixed distance of 500 μm using a Leica microtome CM 1850 Cryostat (temperature at −19° C.) and mounted on Thermo Polysine slides (Thermo Scientific, Cat J2800AMNZ). The collected sections represented a total distance of ~5-6 mm, and covered the whole thyroid region of each animal. The tissue sections were then stained with hematoxylin-eosin (HE) and examined using bright field illumination on a Zeiss upright microscope. Thyroid volumes ($mm^3$) were calculated from the sum of the areas of each section over the whole cutting region. Myocardial volumes ($mm^3$) were calculated in a similar way as described for thyroid glands from the sum of the areas of each section over whole cutting region (5 to 6 slides, depending on respective size of the hearts). The method has been described before (22). For orbital preparations, complete dissections of the orbital and periorbital areas were carried out, thus collecting all orbital tissues, eyelids and adjacent tissues. Consecutively, the tissues were trimmed, fixed, and decalcified by placing in EDTA solution (15%, pH of 7.0) for 48 hours, then washed 3× with PBS. Then, the tissues were immerged into a sucrose solution (30% in PBS) for 24 h at 4° C., followed by fine-trimming and incubating in optimum cutting temperature (OCT) formulation (Tissue-Tek® O.C.T.™ compound, VWR Chemicals, Leuven, Belgium) for 5 minutes at room temperature. Special care was taken to embed the optical nerve side upside down. Using the microtome, we carried out serial coronary sections (7 μm thick, 0.63 mm apart), starting cutting at the level at Bregma 0 and collecting sections at the positions (compared to Bregma) of +0.63, +1.26, +1.89, +2.52, +3.15, +3.78, +4.41, and +5.04 mm (FIG. 6A). Sections were stored at −70° C. until use. Then, they were thawed to room temperature for 30 min, and stained with HE. For Masson's staining, sections were placed in Bouin's fixation solution (containing 30 mL saturated picric acid, 10 mL concentrated formaldehyde, 2 ml glacial acetic acid) at 20° C. overnight and washed under running tap water for 2 hours. Then, sections were treated with Masson-Goldner trichrome staining kit (Roth, Germany, cat. No. 3459.1) according to the provider's protocol.

The orbital sections were viewed at 4× objective lens (Axioscope, Zeiss), captured with an Axiovision digital cam system and recorded with 2560×1920 pixel resolution. Focus was adjusted for each new field, but light conditions were kept identical. All sections were evaluated in a blinded fashion.

Fibrosis areas in the extra-orbital adipose tissue and extra-orbital muscle (EOM) regions were indicated by their green colour. Digitized image analysis of green colour pixels was carried out using the luminescence tool of Adobe Photoshop software version CS5 extended on the basis of pixel areas. In order to correct for possible bias between stainings, the green staining intensity of the respective orbital bone in each section was taken as an internal standard for each measurement. Quantification of fibrosis by digitized Adobe Photoshop analysis of Masson's trichrome stains had been validated previously (25). Accordingly, all fibrotic tissue throughout a whole orbital section was quantified, and results of all sections were added in the end to yield a total fibrosis volume ($mm^3$) of each investigated orbita (taking account of the 0.63 mm interval thicknesses between sections).

In Vitro Studies

In order to investigate the direct binding of peptides to anti-TSHR antibodies, Roche's Cobas® assay (04388790) for ECLIA was used with minor modifications: 30 μl of the diluted monoclonal M22-Bio antibody was mixed with 30 μl diluted peptide or TSHR-Fc (final concentration of 100 μg/ml in PBS) and added to the TSHR-pre-coated microtiter plate. After an incubation step for 2 h at room temperature the protocol was continued according to the manufacturer's instructions.

To investigate effects on TSHR-dependent cAMP stimulation ex vivo, TSHR-overexpressing CHO cells JP2626 were prepared as described above. Then, 100 μg/ml peptide 829, peptide of the invention 836 or fusion protein TSHR-Fc were added to the JP2626 cells. After incubation for 2.5 hours at 37° C. the cAMP release in the medium was measured in duplicates by a competitive immunoassay ELISA (#EMSCAMPL, Thermo Fisher Scientific, Waltham, Mass., USA).

Statistics

Differences between the groups were analysed by ANOVA for comparison between groups using SPSS software (version 19), followed by LSD (least significant difference) post-hoc testing, or Student's t test where appropriate. For comparison of values at various times within one group, ANOVA for repeated measurements (RM-ANOVA) was used where appropriate.

Results and Discussion

Selection of Cyclic Peptides

Cyclic peptides were synthesized whose amino acid sequences and tertiary structures were derived from each of the ten loops of TSHR leucin-rich domain (LRD) (cf. Table 1 shown above).

Peptide 836 is a 24-meric cyclic peptide corresponding to the eighth TSHR LRD loop, and peptide 829 (also 24-meric) to the first loop of the TSHR LRD. As an example for an inactive control, peptide 835 whose sequence was derived from the $7^{th}$ loop, is included in further results. All three peptides were easily soluble in water, so that 0.9% NaCl was used as vehicle, as well as for TSHR-Fc.

Anti-TSHR Antibody Titers and Capacity to Stimulate cAMP in Test Cells

Anti-TSHR antibodies were determined from serum samples by investigating the ability of the respective mouse sera to inhibit the binding of the monoclonal Graves' patient antibody M22 to the TSHR ("$3^{rd}$ generation ELISA"). Highly significant titers were detected in all Ad-TSHR-immunized animals. In the mock-treated group, mean anti-TSHR antibody titers increased progressively during the course of the study (FIG. 2). In contrast, peptide 836-treated and TSHR-Fc-treated animals showed no trends for further anti-TSHR titer increases after start of therapy despite continuing immunisations, whereas titers in peptide 829-treated mice were similar to those in the untreated control group.

In addition, the stimulatory activity of these antibodies was determined as the capacity of mouse serum samples to induce an increase in TSHR-dependent cAMP levels in test cells (FIG. 3). Anti-TSHR antibodies from almost all TSHR-immunized mice showed potency to stimulate cAMP in TSHR-expressing test cells. The maximum inducible cAMP levels showed considerable variation. Cyclic peptide therapy did not impact on these mean cAMP values. A trend towards somewhat lower TSHR-cAMP stimulation values for peptide 829 might be guessed from FIG. 3. However, the values were not significantly different from controls, and the effect is a random group effect, because it occurred already before start of therapy (it is evident at week 8).

Thyroid Sizes, as Determined Macroscopically and from Histological Sections

Thyroid volumes ($mm^3$) were determined from the sum of the areas of each section over the whole cutting region (between 5 and 10 slides, depending on respective size of the thyroid gland) multiplied by the slice thickness of 0.5 mm. This macroscopic investigation showed clearly increased thyroid sizes in mice which had received 9 immunisations of Ad-TSHR (see FIG. 4B), compared to the healthy mouse group. In contrast, peptide 836-treated and TSHR-Fc-treated animals showed decreased thyroid sizes, whereas peptide 829-treated mice resulted in a trend which did not reach statistical significance. Also other tested cyclic peptides derived from the structure of the TSHR A domain did not show any effects—as an example for an inactive control, results for peptide 835 whose sequence was derived from the $7^{th}$ loop are also shown. FIG. 4A shows representative macro photographs of the thyroids.

Patho-Histological Changes of the Thyroid

Also a qualitative histological investigation was carried out on some animals. In 9×AdTSHR-treated mice, prominent infoldings of the hyperplastic follicular epithelium occurred, which led to fractioning of thyroid follicles, and corresponding smaller follicle and colloid sizes (see reference 22). This degenerate histological image contrasted with the normal aspect of intact follicles and normal colloid size of native animals. Mean histological scores of TSHR-Fc-treated groups were markedly better compared to the vehicle-treated group (Supplement Figure).

Determination of Thyroxin Serum Levels

Thyroxin (T4) levels did not differ between groups at study start, and mean T4 levels in the Ad-TSHR-immunized groups were consistently and significantly higher than controls until week 11 (start of therapy, FIG. 5). Compared to published normal values in mice (serum T4 levels>8 μg/dl were considered hyperthyroid in BALB/c mice by most authors), T4 levels were consistently increased beyond that cut-off value in these groups. After start of therapy, peptide 836-treated and TSHR-Fc-treated animals showed progressively decreasing T4 levels, which consecutively reverted to normal values. Mean values were close to the healthy animal group at later time points.

In contrast, comparative peptide 829-treated mice showed a trend which did not reach statistical significance. Also other tested cyclic peptides derived from the structure of the other loops of the leucin-rich TSHR A domain did not result in any effects (as an example for an inactive control, results for peptide 835 whose sequence was derived from the $7^{th}$ loop are also shown).

Patho-Histological Changes of the Orbitae

A histological investigation of retro-orbital fibrosis was carried out on most animals. Coronary sections of orbital and retro-orbital tissues were evaluated after Masson's staining (see FIG. 6A). In 9×AdTSHR-treated mice, a significant increase of retro-orbital fibrosis was observed upon digitized image analysis (see also ref. 23) which was completely reversed in peptide 836-treated mice (FIG. 6B). Tissues from 4 of the treatment groups were analysed—sections from the other peptide-treated groups were not processed, since these peptides had not improved the other investigated parameters.

ECG to Determine Heart Rates

Starting from the $3^{rd}$ immunisation, a significant increase in heart rate in the hyperthyroid Ad-TSHR immunized group was observed (FIG. 7A). In contrast, heart rate in the native, healthy group was only mildly increased at older age, but did not change significantly.

Upon consecutive Ad-TSHR-immunizations, a further strong increase in heart rate in the hyperthyroid vehicle-treated group was observed. In contrast, peptide 836-treated and TSHR-Fc-treated animals showed no further increase, and significantly decreased resting heart rates at later time points. The mean heart rates of these two treated groups showed mean values close to the healthy animal group. In contrast, peptide 829-treated mice showed a trend which did not reach statistical significance. Also other tested cyclic peptides derived from the structure of the TSHR A domain did not show any effects—as an example for an inactive control, please see results for peptide 835.

Heart Weights

Macroscopical investigation and preparation of mouse hearts upon necropsy revealed significantly increased heart weights in the Ad-TSHR-immunized groups (FIG. 7B). In contrast, peptide 836-treated animals showed significantly reduced heart weights. Peptide 829-treated and TSHR-Fc-treated animals showed trends towards reduced heart weights which did not reach statistical significance. Also other tested cyclic peptides derived from the structure of the TSHR A domain did not show any effects—as an example for an inactive control, please see results for peptide 835. Additionally, calculation of myocardial volumes by adding up digitized cross-sectional LV areas from 6 consecutive sections, which were evenly distributed across the fixated hearts, showed increased LV volumes in vehicle-treated mice. In contrast, peptide 836-treated and TSHR-Fc-treated animals showed significantly reduced ventricular myocardial volumes (FIG. 7C). Due to unavailability of some fine histological sections, analysis of this parameter in mice treated with other peptides could unfortunately not be completed.

Studies in Immunologically Naive Mice

All immunologically naïve mice tolerated 6 monthly administrations of either 1 mg/kg bw cyclic peptide 836 or vehicle (NaCl) equally well—no pathological clinical findings were observed. Generation of anti-TSHR antibodies was not observed in any of the 6 animals treated with cyclic peptide 836 over 6 months—all measured titers were below background, so that no immune response to either peptide was documented. Because of lacking efficacy in the disease model, administration of peptide 829 in naïve mice was omitted.

In contrast, one naïve mouse which was treated with 1 mg/kg bw TSHR-Fc developed clinical signs of allergy immediately after 4 administrations. In this mouse and two other mice treated with 1 mg/kg TSHR-Fc (total: 3 out of 6 TSHR-Fc-treated naïve mice), anti-TSHR antibody titers above cut-off limit (as defined in the control groups) occurred after 3 administrations, and were further observed upon continuing monthly measurements. At the end of the 6 month observation period, average anti-TSHR antibody titers in all naïve mice which had received TSHR-Fc were significantly ($p<0.001$) higher than in cyclic peptide-treated or vehicle-treated control mice.

In Vitro Studies

In order to investigate whether the cyclic peptides or TSHR-Fc had a direct, scavenging effect on anti-TSHR antibodies, we used a modified 3rd generation titer assay. Results are shown in FIG. 8A: The fusion protein TSHR-Fc (100 μg/mL) significantly reduced anti-TSHR antibody titers (as determined by measuring M22 binding, which was added at a final concentration of 10 ng/mL, to its substrate), whereas no such effect was observed with the cyclic peptides. Also, we investigated the cAMP-stimulating potencies in TSHR-expressing test cells, yielding qualitatively comparable results (FIG. 8B).

The invention claimed is:

1. A cyclic peptide, wherein the peptide is of formula (I)

$$\text{cyclo}(x_{(i)}\text{GYAFNGTKLDAVYLNKNKYLTVID (SEQ ID NO: 1))} \quad \text{(I)}$$

wherein x is at each occurrence individually selected from an amino acid;

i is an integer from 0 to 5.

2. The cyclic peptide according to claim 1, wherein i=0.

3. A pharmaceutical composition comprising the cyclic peptide according to claim 1, and optionally a pharmaceutically acceptable carrier.

4. A cyclic peptide according to claim 1 for use in the treatment, amelioration or prevention of a disease caused by antibodies targeting the thyrotropin-TSH receptor (TSHR) in the thyroid gland.

5. A cyclic peptide according to claim 1 for use in the treatment, amelioration or prevention of Graves' disease and/or Graves' orbitopathy as well as cardiovascular symptoms associated therewith.

6. A pharmaceutical composition of claim 3 for use in the treatment, amelioration or prevention of a disease caused by antibodies targeting the thyrotropin-TSH receptor (TSHR) in the thyroid gland.

7. A pharmaceutical composition of claim 3 for use in the treatment, amelioration or prevention of Graves' disease and/or Graves' orbitopathy as well as cardiovascular symptoms associated therewith.

* * * * *